United States Patent
Friedrich et al.

(10) Patent No.: US 9,776,951 B2
(45) Date of Patent: Oct. 3, 2017

(54) POLYGLYCEROL ESTERS WITH A PARTICULAR OLIGOMER DISTRIBUTION OF THE POLYGLYCEROL

(71) Applicant: Evonik Degussa GmbH, Essen (DE)

(72) Inventors: Achim Friedrich, Hattingen (DE); Jürgen Meyer, Essen (DE); Jan Marian von Hof, Essen (DE); Oliver Springer, Wesel (DE); Peter Muss, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/113,993

(22) PCT Filed: Feb. 11, 2015

(86) PCT No.: PCT/EP2015/052812
§ 371 (c)(1),
(2) Date: Jul. 25, 2016

(87) PCT Pub. No.: WO2015/132053
PCT Pub. Date: Sep. 11, 2015

(65) Prior Publication Data
US 2016/0340290 A1    Nov. 24, 2016

(30) Foreign Application Priority Data
Mar. 4, 2014 (DE) .................. 10 2014 203 868

(51) Int. Cl.
| | | |
|---|---|---|
| C07C 51/00 | (2006.01) | |
| C07C 69/33 | (2006.01) | |
| A61Q 15/00 | (2006.01) | |
| A61Q 17/04 | (2006.01) | |
| A61Q 19/00 | (2006.01) | |
| B01F 17/00 | (2006.01) | |
| A61K 8/39 | (2006.01) | |
| A61Q 1/02 | (2006.01) | |
| A61K 8/06 | (2006.01) | |
| C07C 67/08 | (2006.01) | |

(52) U.S. Cl.
CPC .............. *C07C 69/33* (2013.01); *A61K 8/06* (2013.01); *A61K 8/062* (2013.01); *A61K 8/39* (2013.01); *A61Q 1/02* (2013.01); *A61Q 15/00* (2013.01); *A61Q 17/04* (2013.01); *A61Q 19/00* (2013.01); *A61Q 19/007* (2013.01); *B01F 17/0028* (2013.01); *C07C 67/08* (2013.01)

(58) Field of Classification Search
CPC ...................................................... C07C 69/33
USPC ........................................................ 554/173
See application file for complete search history.

(56) References Cited

U.S. PATENT DOCUMENTS

| | | | |
|---|---|---|---|
| 8,466,248 B2 | 6/2013 | Meyer et al. | |
| 8,653,289 B2 | 2/2014 | Wenk et al. | |
| 9,427,385 B2 * | 8/2016 | Meyer | A61Q 17/04 |
| 2012/0156271 A1 | 6/2012 | Matsuzawa et al. | |
| 2014/0072521 A1 | 3/2014 | Meyer et al. | |

FOREIGN PATENT DOCUMENTS

| | | |
|---|---|---|
| DE | 102008001788.4 A1 | 11/2009 |
| EP | 2363387 A2 | 9/2011 |
| EP | 2705832 A2 | 3/2014 |
| JP | 2003104852 A | 4/2003 |
| JP | 2006055029 A | 3/2006 |
| JP | 2010178723 A | 8/2010 |
| WO | 2008103289 A1 | 8/2008 |
| WO | 2012127129 A1 | 9/2012 |

OTHER PUBLICATIONS

German language International Search Report mailed on Apr. 28, 2015 in PCT/EP2015/052812 (4 pages).
German language Written Opinion mailed on Apr. 28, 2015 in PCT/EP2015/052812 (6 pages).
International Search Report mailed on Apr. 28, 2015 in PCT/EP2015/052812 (3 pages).

* cited by examiner

*Primary Examiner* — Deborah D Carr
(74) *Attorney, Agent, or Firm* — Philip P. McCann; Smith Moore Leatherwood LLP

(57) ABSTRACT

The invention relates to novel polyglycerol esters with a particular oligomer distribution of the polyglycerol present, and to their use in particular in cosmetic formulations as, for example, emulsifier.

19 Claims, No Drawings

POLYGLYCEROL ESTERS WITH A PARTICULAR OLIGOMER DISTRIBUTION OF THE POLYGLYCEROL

This application is a national stage application under 35 U.S.C. §371 of International Application No. PCT/EP2015/052812 filed 11 Feb. 2015, which claims priority to German Application No. 10 2014 203 868.5 filed 4 Mar. 2014, the disclosures of which are expressly incorporated herein by reference.

FIELD OF THE INVENTION

The invention relates to novel polyglycerol esters with a particular oligomer distribution of the polyglycerol, and to the use thereof in particular in cosmetic formulations.

BACKGROUND

In recent years, a major trend towards products based on renewable raw materials has been pursued in the cosmetics market. In order to be able to satisfy this, it is necessary to be able to offer high-performance emulsifiers based on renewable raw materials. Customary emulsifiers in cosmetics often comprise as hydrophilic groups polyethylene glycol groups (PEG), which can be produced by polymerization of ethylene oxide obtained by petrochemical means. Since all of the raw materials used in formulations that are as natural as possible should originate from renewable sources, PEG-containing emulsifiers are not desired in such formulations. Polyglycerol esters are a preferred PEG-free alternative for cosmetic emulsifiers based on renewable raw materials.

The use of polyglycerol esters in cosmetics as emulsifier is well-known technology. For example, JP 2003104852 describes the use of a polyglycerol behenate stearate that is solid at room temperature in hair care products.

JP 2010178723 describes the use of polyglycerol partial esters of behenic acid in combination with other, shorter-chain fatty acids as dough improvers in bakery goods.

JP 2006055029 describes the use of triglycerol monobehenate monostearate in crop protection applications.

EP2363387 describes the preparation of polyglycerol carboxylic acid partial esters and the use thereof as emulsifiers in cosmetics.

Using the polyglycerol esters described in the prior art it is not possible to produce stable emulsions with a good skin feel despite low viscosity, particularly in conjunction with high microbiological stability.

It was an object of the invention to provide an emulsifier which was able to overcome at least one disadvantage of the prior art.

SUMMARY

Surprisingly, it has been found that the polyglycerol esters described below are able to solve the problem addressed by the invention.

The present invention therefore provides polyglycerol esters as described in Claim 1 and claims dependent thereon.

The invention further provides a process for producing the polyglycerol esters according to the invention, and the use thereof as emulsifier or for aiding the microbiological stabilization of formulations and formulations which comprise these.

One advantage of the present invention is that the provided emulsifier based on the polyglycerol ester according to the invention is based completely on renewable raw materials.

Another advantage of the present invention is that the provided emulsifier based on the polyglycerol ester according to the invention is suitable for the formulation of O/W emulsions (creams, lotions) with excellent storage stability.

A further advantage of the present invention is that the provided emulsifier based on the polyglycerol ester according to the invention is suitable for the formulation of PEG-free emulsions, in particular thin-liquid PEG-free emulsions.

A further advantage of the present invention is that the provided emulsifier based on the polyglycerol ester according to the invention is suitable for the formulation of antiperspirant and/or deodorant formulations. It is particularly advantageous here that deodorant systems can also be produced without aluminum salts. Furthermore, it is particularly advantageous that the antiperspirant and/or deodorant formulations can be PEG-free.

Emulsions and formulations comprising such emulsifier based on the polyglycerol ester according to the invention moreover have a good skin feel.

The emulsifier based on the polyglycerol ester according to the invention can stabilize emulsions against emulsion-burdening ingredients. Here, mention is made for example of sunscreen formulations comprising UV filters, electrolyte-containing formulations and formulations with cosmetic active ingredients, and in particular pigment-containing emulsions.

Advantageously, emulsions and formulations comprising such emulsifier based on the polyglycerol ester according to the invention do not necessarily require paraben-containing preservatives, but can also be microbially stabilized using other preservatives.

Typical preservatives are substances listed in Annex VI of the EU Cosmetics Ordinance (76/768/EEC), such as e.g. phenoxyethanol, methylisothiazolinones and benzoic acid.

In this connection, it is a further advantage of the present invention that the polyglycerol esters according to the invention can intensify the effect of the preservatives.

It is a further advantage of the present invention that the provided emulsifier is suitable for the formulation of emulsions without polyacrylate-based thickeners.

It is a further advantage of the present invention that the provided emulsifier can be handled easily on account of its consistency.

It is a further advantage of the present invention that the provided emulsifier produces a light skin feel in formulations.

It is a further advantage of the present invention that the use of the provided emulsifier imparts moisturizing properties to the formulations.

The composition of natural raw materials, and the ability of the emulsifier based on the polyglycerol ester according to the invention to stabilize emulsions even without polyacrylate-based thickeners permits the production of natural emulsions corresponding to the criteria of certification organizations for natural cosmetics, such as for example Natrue, Ecocert or Cosmos. The light skin feel and the moisturizing properties of the polyglycerol emulsifiers according to the invention recommend the use of these in sera, moisturizing lotions, antiageing formulations or blemish balm creams (tinted active ingredient formulation).

It is a further advantage of the present invention that the use of the provided emulsifier imparts good compatibility with UV filters to the formulations.

It is a further advantage of the present invention that the use of the provided emulsifier gives the formulations good effectiveness as regards incorporated preservatives, such as e.g. phenoxyethanol.

It is a further advantage of the present invention that the use of the provided emulsifier gives the formulations good emulsion stability even in the presence of the incorporated preservatives. Of particular advantage here is the good stability even at low pH values, which are required in order to achieve a microbiological stability of the cosmetic emulsions using natural preservatives such as, for example, benzoic acid or sorbic acid.

DETAILED DESCRIPTION

A polyglycerol ester is therefore claimed which, after its complete hydrolysis, releases on average (number-average) per mole of polyglycerol ester from 1.1 to 4 mol, preferably from 1.2 to 3 mol, particularly preferably 1.3 to 2.7 mol, of at least one carboxylic acid having 8 to 24 carbon atoms, characterized in that, after complete hydrolysis of the polyglycerol ester, a polyglycerol is obtained in which the mass ratio of glycerol to diglycerol is greater than 1.5, preferably greater than 2, particularly preferably greater than 3.

Preferably, the aforementioned mass ratio of glycerol to diglycerol is less than 15.

Preferred polyglycerol esters according to the invention are characterized in that, after their complete hydrolysis, on average (number-average) per mole of polyglycerol ester from 0.1 to 1.5 mol, preferably from 0.2 to 1.0 mol, particularly preferably from 0.3 to 0.7 mol, of at least one first carboxylic acid having 14 to 24, preferably 16 to 20, in particular 16 to 18, carbon atoms and from 0.5 to 3.9 mol, preferably from 0.8 to 2.5 mol, particularly preferably from 1.0 to 2.0 mol, of at least one second carboxylic acid having 6 to 12, preferably having 8 to 10, particularly preferably 8, carbon atoms are released.

In the context of the present invention, the term "polyglycerol" is to be understood as meaning a polyglycerol which comprises glycerol. Consequently, for the purposes of calculating amounts, masses and the like, the glycerol fraction should also be taken into consideration. In the context of the present invention, polyglycerols are therefore mixtures comprising glycerol and at least one glycerol oligomer. Glycerol oligomers are to be understood in each case as meaning all corresponding structures, e.g. thus linear and cyclic compounds.

The same applies for the term "polyglycerol ester" in connection with the present invention.

The stated number-average of the acid radicals refers in the case of more than one of the first and/or second carboxylic acid in each case to the accumulated sum of all of the first and/or second acid radicals.

Unless stated otherwise, all of the stated percentages (%) are percent by mass.

The mass fraction of glycerol, diglycerol, triglycerol, and of the fatty acids can be determined for the purposes of the present invention by two GC methods; these methods include the alkaline hydrolysis of the polyglycerol ester according to the invention, separation of the polyglycerol from the resulting acids and analysis of the fatty acids, and also of the glycerol oligomers (linear and cyclic).

For this, 0.5 g of the polyglycerol ester according to the invention are boiled in 25 ml of an ethanolic 0.5 M KOH solution under reflux for 4 hours. Then, 10 ml of water are added and the pH is adjusted to pH 2-3 with sulphuric acid. The resulting carboxylic acids are separated off by means of triple extraction with in each case one volume (30 ml) of petroleum ether.

Fatty Acid Analysis:

The combined extracts are concentrated to about 1 ml by evaporation.

Suitable determination methods for ascertaining the fatty acid distribution are in particular those according to DGF C VI 11a, DGF C-VI 10 a and GAT—ring test 7/99.

A 0.5 ml aliquot of the petroleum ether extract obtained as described above is admixed in a vessel with 1 ml of a mixture of acetyl chloride:methanol (1:4) and 1 ml of chloroform and analysed by means of GC. This is carried out in a gas chromatograph, which is equipped with a split/splitless injector, a capillary column and a flame ionization detector, under the following conditions:

Injector: 290° C., split 30 ml
Injection volume: 1 µl
Column: 30 m*0.32 mm HP1 0.25 µm
Carrier gas: Helium, constant flow, 2 ml/min
Temperature programme: 80° C.-300° C. at 4° C./min, then conditioning for 10 minutes at 300° C.
Detector: FID at 320° C.
Hydrogen 35 ml/min
Air 240 ml/min
Make Up gas 12 ml/min The carboxylic acids are separated as their methyl esters according to their carbon chain length and their mass fraction is determined according to an internal standard method. For this, the GC system is calibrated by measuring fatty acid methylester mixtures of the fatty acids to be investigated with known composition.

Using this method, the total mass and the mass fractions of carboxylic acid(s) are obtained, which permit a determination of the quantitative amount(s) by using the respective molecular weight. The total mass of carboxylic acid(s) can moreover be used to determine, by means of subtraction, the mass of polyglycerol present, for example, in 0.5 g of polyglycerol ester. Using the molecular weight of the polyglycerol, the quantitative amount of the polyglycerol can be determined therefrom.

$M_p = 74 \cdot N + 18$ where $M_p$ = molecular weight of the polyglycerol [g/mol]
$N$ = degree of polymerization of the polyglycerol (as regards the determination of the degree of polymerization, see below).

$n_p = \dfrac{m_p}{M_p}$ where $n_p$ = quantitative amount of the polyglycerol [mol] in 1 g of polyglycerol ester
$m_p$ = mass of polyglycerol in 1 g of polyglycerol ester [g]
$M_p$ = molecular weight of the polyglycerol [g/mol]

Together, the molar ratios of polyglycerol to carboxylic acids can be determined from these values.

Analysis of Glycerol, Diglycerol and Triglycerol:

The residue extracted with petroleum ether is adjusted with barium hydroxide to pH 7 to 8. The precipitated barium sulphate is separated off by centrifugation.

The supernatant is drawn off and the residue is extracted three times with 20 ml of ethanol.

The combined supernatants are concentrated for 30 min at 80° C. and 50 mbar and dried.

For the analysis of glycerol, diglycerol and triglycerol by means of GC, the residue is dissolved in 2 ml of pyridine: chloroform (4:1). 0.5 ml of this solution is admixed with 1 ml of MSTFA [N-methyl-N-(trimethylsilyl)trifluoroacetamide]. The alcohols are quantitatively converted to their trimethyl silyl ethers by reaction at 80° C. (30 minutes) and then analysed by means of GC/FID.

This is carried out in a gas chromatograph, which is equipped with a split/splitless injector, a capillary column and a flame ionization detector, under the following conditions:

Injector: 290° C., split 30 ml
Injection volume: 1 µl
Column: 30 m*0.32 mm HP1 0.25 µm
Carrier gas: Helium, constant flow, 2 ml/min
Temperature programme: 80° C.-300° C. at 4° C./min, then conditioning for 10 minutes at 300° C.
Detector: FID at 310° C.
  Hydrogen 35 ml/min
  Air 240 ml/min
  Make Up gas 12 ml/min Glycerol, diglycerol and triglycerol are separated and their mass fraction is determined by an internal standard method. For this, the GC system is calibrated by measuring mixtures of the glycerols to be investigated and of the internal standard with known composition.

The mass fractions can be used to determine the mass ratio of glycerol to diglycerol and, by subtraction from 100%, also the content of polyglycerols with a degree of polymerization of 2 and greater (100% minus mass fraction of the glycerol), the content of polyglycerols with a degree of polymerization of 3 and greater (100% minus mass fractions of the glycerol and of the diglycerols) and the content of polyglycerols with a degree of polymerization of 4 and greater (100% minus mass fractions of the glycerol, the diglycerols and the triglycerols).

Should glycerol, but no detectable amount of diglycerol be present in a polyglycerol under consideration, then this corresponds to a mass ratio of glycerol to diglycerol of greater than 3.

It is preferred according to the invention that the polyglycerol obtained after complete hydrolysis of the polyglycerol ester according to the invention has an average degree of polymerization of from 1.5 to 10, preferably from 1.7 to 6, particularly preferably from 2 to 3.5

The average degree of polymerization of the polyglycerol N is calculated via its hydroxyl number (OHV, in mg KOH/g) according to the following formula:

$$N = \frac{(112200 - 18 \cdot OHV)}{(74 \cdot OHV - 56100)}$$

Suitable methods for determining the hydroxyl number are particularly those according to DGF C-V 17 a (53), Ph. Eur. 2.5.3 Method A and DIN 53240.

It is preferred according to the invention that the polyglycerol obtained after complete hydrolysis of the polyglycerol ester according to the invention comprises at least 50% by weight, preferably at least 60% by weight, of polyglycerols with a degree of polymerization of 2 and greater, where the percentages by weight refer to the total content of polyglycerol.

It is preferred according to the invention that the polyglycerol obtained after complete hydrolysis of the polyglycerol ester according to the invention comprises at least 40% by weight, preferably at least 50% by weight, of polyglycerols with a degree of polymerization of 3 and greater, where the percentages by weight refer to the total content of polyglycerol.

It is preferred according to the invention that the polyglycerol obtained after complete hydrolysis of the polyglycerol ester according to the invention comprises at least 30% by weight, preferably at least 40% by weight, of polyglycerols with a degree of polymerization of 4 and greater, where the percentages by weight refer to the total content of polyglycerol.

It is particularly preferred according to the invention that the polyglycerol obtained after complete hydrolysis of the polyglycerol ester according to the invention comprises at least 50% by weight, preferably at least 60% by weight, of polyglycerols with a degree of polymerization of 2 and greater, at least 40% by weight, preferably at least 50% by weight, of polyglycerols with a degree of polymerization of 3 and greater and at least 30% by weight, preferably at least 40% by weight, of polyglycerols with a degree of polymerization of 4 and greater, where the percentages by weight refer to the total content of polyglycerol.

Advantageous polyglycerol esters according to the present invention are characterized in that the molar ratio of the first carboxylic acids obtained after complete hydrolysis of the polyglycerol ester to the second carboxylic acid is between 1:1.5 and 1:5.0, preferably between 1:2.0 and 1:4.0, particularly preferably between 1:2.5 and 1:3.0.

The method for determining the molar ratios that can be used is the method described above.

It is preferred according to the invention that the first and the second carboxylic acid of the polyglycerol ester is selected from fatty acids, these being in particular selected from linear, saturated, unsubstituted carboxylic acids.

Fatty acids that can be used both for the first and the second carboxylic acid are mixtures of fatty acids, it being preferred for the first carboxylic acid that it is a mixture in this connection. This is naturally grounded in the nature of the production process in which preferably technical-grade mixtures of fatty acids are used.

A polyglycerol ester preferred according to the invention is characterized in that it comprises, as the first carboxylic acid, one selected from stearic acid and palmitic acid, and also mixtures thereof. Preferred mixtures can be varied widely in the weight ratio of stearic acid to palmitic acid from 100:0.01 to 0.01:100. Here, preference is given to a C18:C16 weight ratio of 30:70 to 95:5, particularly a ratio of 45:55 to 90:10.

A preferred second carboxylic acid is caprylic acid.

A particularly preferred embodiment of the polyglycerol ester according to the invention is characterized in that the first carboxylic acid is a mixture of stearic acid and palmitic acid which preferably has a weight ratio in a range from 0.8:1 to 1.2:1, and the second carboxylic acid is caprylic acid.

The polyglycerol esters of the present invention can be produced by classic esterification processes, preferably by the process according to the invention described below.

The present invention further provides a process for producing a polyglycerol ester comprising the process steps A) provision of a polyglycerol in which the mass ratio of glycerol to diglycerol is greater than 1.5, preferably greater than 2, particularly preferably greater than 3,
B) esterification of at least one part of the polyglycerol with at least one carboxylic acid having 8 to 24 carbon atoms, where the molar ratio of the carboxylic acid used in process step B) to polyglycerol used in process step A) is from 1.1:1 to 4:1, preferably from 1.2:1 to 3:1, particularly preferably 1.3:1 to 2.7:1.

Preferred processes according to the invention are characterized in that in process step B) at least one first carboxylic acid having 14 to 24 carbon atoms and at least one second carboxylic acid having 6 to 12 carbon atoms are used, where the molar ratio of the first carboxylic acid used in process step B) to polyglycerol used in process step A) is from 0.1:1 to 1.5:1, preferably from 0.2:1 to 1.0:1, particularly preferably from 0.3:1 to 0.7:1, and the molar ratio of the second carboxylic acid used in process step B) to polyglycerol used in process step A) is from 0.5:1 to 3.9:1, preferably from 0.8:1 to 2.5:1, particularly preferably from 1.0:1 to 2.0:1.

The polyglycerol for process step A) can be provided by different conventional methods such as, for example, polymerization of glycidol (e.g. base-catalyzed), polymerization of epichlorohydrin (for example in the presence of equimolar amounts of a base such as NaOH) or polycondensation of glycerol.

According to the invention, preference is given to the provision of the polyglycerol by the condensation of glycerol, in particular in the presence of catalytic amounts of a base, in particular NaOH or KOH. Suitable reaction conditions are temperatures between 220 and 260° C. and reduced pressure in a range between 20 and 800 mbar, in particular between 50 and 500 mbar, as a result of which facilitated water removal is possible. Corresponding processes can be found in standard chemistry textbooks such as, for example, Römpp.

It may be advantageous to bring a conventionally obtained polyglycerol to the ratio of glycerol to diglycerol required according to the invention by admixing glycerol.

It is preferred if the polyglycerol provided in process step A) has an average degree of polymerization of from 1.5 to 10, preferably from 1.7 to 6, particularly preferably from 2 to 3.5.

It is preferred according to the invention if the polyglycerol provided in process step A) comprises at least 50% by weight, preferably at least 60% by weight, of polyglycerols with a degree of polymerization of 2 and greater, where the percentages by weight refer to the total content of polyglycerol.

It is preferred according to the invention if the polyglycerol provided in process step A) comprises at least 40% by weight, preferably at least 50% by weight, of polyglycerols with a degree of polymerization of 3 and greater, where the percentages by weight refer to the total content of polyglycerol.

It is preferred according to the invention if the polyglycerol provided in process step A) comprises at least 30% by weight, preferably at least 40% by weight, of polyglycerols with a degree of polymerization of 4 and greater, where the percentages by weight refer to the total content of polyglycerol.

It is particularly preferred according to the invention if the polyglycerol provided in process step A) comprises at least 50% by weight, preferably at least 60% by weight, of polyglycerols with a degree of polymerization of 2 and greater, at least 40% by weight, preferably at least 50% by weight, of polyglycerols with a degree of polymerization of 3 and greater and at least 30% by weight, preferably at least 40% by weight, of polyglycerols with a degree of polymerization of 4 and greater, where the percentages by weight refer to the total content of polyglycerol.

In the process according to the invention, the process steps B) are carried out under conditions known to the person skilled in the art for esterification reactions, optionally in the presence of a catalyst. In particular, this esterification is carried out with removal of water from the reaction mixture.

Process step B) is preferably carried out at 180-260° C., particularly preferably at 210-250° C.

The course of the reaction can be monitored for example via the acid number of the product, meaning that it is preferred in process step B) to carry this out until the desired acid number is reached.

Preferably, in process step B), the first and the second carboxylic acid are used in a molar ratio between 1:1.5 and 1:5.0, preferably between 1:2.0 and 1:4.0, particularly preferably between 1:2.5 and 1:3.0.

The first and second carboxylic acids used in process step B) in the process according to the invention are preferably those which have been mentioned above as preferred in polyglycerol esters according to the invention.

In particular, in this connection, the first carboxylic acid used is a mixture of stearic acid and palmitic acid which preferably has a weight ratio of stearic acid to palmitic acid in a range from 0.8:1 to 1.2:1, and the second carboxylic acid used is caprylic acid.

Polyglycerol esters according to the invention and polyglycerol esters obtainable or obtained by the process according to the invention are exceptionally suitable for use as a high-performance O/W emulsifier which is based exclusively on renewable raw materials and has a large formulation flexibility, in particular in cosmetic formulations.

Consequently, emulsifiers comprising polyglycerol esters according to the invention or polyglycerol esters obtainable or obtained by the process according to the invention are the subject of the present invention. In the context of this invention, an emulsifier is understood as meaning an emulsifier which consists at least of a polyglycerol ester according to the invention or polyglycerol ester obtainable or obtained by the process according to the invention and optionally at least one coemulsifier, with the presence of a coemulsifier being preferred.

The coemulsifiers used can advantageously be the following coemulsifiers: Polyglyceryl-3 dicitrate/stearate, Polyglyceryl-3 methylglucose distearate, Polyglyceryl-10 stearate, Polyglyceryl-6 distearate, methylglucose sesquistearate, sodium stearoyl glutamate, sodium cetearyl sulfate, potassium cetyl phosphate, glyceryl stearate citrate, cetearyl glucoside, glyceryl stearate, glyceryl stearate SE, cetearyl alcohol and stearic acid.

Likewise, polyglycerol esters according to the invention and polyglycerol esters obtainable or obtained by the process according to the invention are exceptionally suitable for use for producing cosmetic or pharmaceutical formulations, in particular for producing cosmetic creams and lotions.

In this connection, creams and lotions are understood as meaning cosmetic O/W emulsions with spreadable-pasty or flowable consistency.

In general, the polyglycerol esters according to the invention can be used for example in care creams and lotions for face, body and hands, in sunscreen emulsions, in sera, in BB creams, in deodorants, in make-up, in aerosols, roll-ons, pump sprays, sticks e.g. in the antiperspirant/deodorant sector, in baby care products, in intimate care products, foot care products, hair care products, nail care products, dental care products or oral care products, and also in dermatological ointments.

Consequently, cosmetic or pharmaceutic formulations, in particular O/W formulations, comprising polyglycerol esters according to the invention or polyglycerol esters obtainable or obtained by the process according to the invention are likewise provided by the present invention. Formulations preferred according to the invention are sunscreen preparations, electrolyte-containing emulsions, formulations containing cosmetic active ingredients and O/W make-up formulations.

Formulations preferred according to the invention comprise the polyglycerol ester according to the invention or polyglycerol ester obtainable or obtained by the process according to the invention in amounts of from 0.01 to 10% by weight, preferably 0.05 to 8% by weight and particularly preferably 0.1 to 7% by weight, based on the total formulation.

In particular, preference is given to cosmetic or pharmaceutical formulations which are essentially free from alkoxylated compounds. The term "essentially free from alkoxylated compounds" in connection with the present invention is to be understood as meaning that the formulations have no notable amounts of alkoxylated compounds which exert a surface-active effect. This is particularly understood to mean that these compounds are present in amounts of less than 1% by weight, preferably less than 0.1% by weight, particularly preferably less than 0.01% by weight, based on the total formulation, in particular no detectable amounts.

The formulations according to the invention can comprise e.g. at least one additional component selected from the group of
  emollients,
  coemulsifiers,
  thickeners/viscosity regulators/stabilizers,
  antioxidants,
  hydrotropes (or polyols),
  solids and fillers,
  pearlescence additives,
  deodorant and antiperspirant active ingredients,
  insect repellents,
  self-tanning agents,
  preservatives,
  conditioners,
  perfumes,
  dyes,
  pigments,
  cosmetic active ingredients,
  care additives,
  superfatting agents,
  solvents,
  UV filters,
  electrolytes,
  multifunctional additives,
  moisturizing substances.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts of these components used, reference is made expressly to the relevant handbooks known to the person skilled in the art, e.g. K. Schrader, "Grundlagen and Rezepturen der Kosmetika [Fundamentals and Formulations of Cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

Since the polyglycerol esters according to the invention can keep pigments or solid bodies extremely stable in emulsion preparations, solids and fillers, in particular particles and additives which are used to achieve a specific skin feel, such as e.g. silicone elastomers, PMMA particles, PE particles, PS particles, nylon particles, boron nitride, starch, cellulose, mica and talc, are a preferred additional component.

Besides the stated particles, it is also possible for insoluble UV filters in the form of pigments, namely finely dispersed metal oxides or salts, to be advantageously present, such as for example titanium dioxide, zinc oxide, iron oxide, aluminum oxide, cerium oxide, zirconium oxide, silicates (talc), barium sulphate and zinc stearate. The particles here should have an average diameter of less than 100 nm, e.g. between 5 and 50 nm and in particular between 15 and 30 nm. They can have a spherical shape, although it is also possible to use those particles which have an ellipsoidal shape or a shape which deviates in some other way from the spherical form. A relatively new class of light protection filters is micronized organic pigments, such as for example 2,2'-methylenebis{6-(2H-benzotriazol-2-yl)-4-(1,1,3,3-tetramethylbutyl)phenol} with a particle size of <200 nm, which is obtainable e.g. as 50% strength aqueous dispersion.

The present invention is likewise very particularly advantageously suitable for stabilizing cosmetic formulations containing color pigments.

Consequently a preferred cosmetic or pharmaceutical formulation comprises, as additional component, a substance selected from the group of the substances of the cosmetic color pigments.

Cosmetic color pigments in connection with the present invention are in particular selected from the group consisting of metal oxides or mixtures thereof, with iron oxides being particularly preferred.

The use of the emulsifier in formulations with electrolytes or ionic compounds is likewise an advantageous area of application. So-called multifunctional additives, which inter alia can have a moisturizing, preserving, viscosity-regulating, emulsifying, stabilizing effect, can likewise be formulated very readily with the emulsifier according to the invention into O/W emulsions, particularly into lotions, for which reason representatives of this substance group are likewise a preferred additional component.

Since the polyglycerol esters according to the invention are able to stabilize emulsions also without the use of polyacrylate-based thickeners, PEG-free and/or silicone-free and/or polyacrylate-free and/or paraben-free formulations based on natural ingredients are a particularly preferred area of application for them.

On account of its moisturizing properties, its light skin feel and the good stabilization of cosmetic active ingredients, polyglycerol esters according to the invention are for example preferably suitable for use in cosmetic emulsions for increasing skin moisture, improving skin structure, reducing age-related changes in the skin, evening out the complexion, promoting skin metabolism or neutralizing harmful metabolic constituents in the skin. Consequently, moisturizing substances and substances with biological efficacy, such as glycerol, urea, peptides, are preferred additional components in preferred formulations according to the invention.

On account of the tolerance of the emulsifiers according to the invention towards different types of preservatives, besides paraben-containing preservatives, it is also possible to readily use paraben-free preservatives such as phenoxyethanol, ethanol or methylisothiazolinone. To produce natural cosmetics, preferred preservatives used are in particular natural acids such as caprylic acid, capric acid, anisic acid, sorbitan acid, levulinic acid, sorbic acid and benzoic acid or substances such as caprylyl glycol, which are used as an additional formulation constituent.

Preferred formulations according to the invention are antiperspirant and/or deodorant formulations. Antiperspirant formulations are characterized in that they have obviously been made in order to prevent the formation of perspiration. Deodorant formulations are characterized in that they have obviously been made in order to prevent the formation of odor. In particular, antiperspirant and/or deodorant formulations comprise active ingredients selected from the group of aluminum salts.

Preferred formulations according to the invention are characterized in that they have a pH of from 3.0 to 7.0, preferably from 3.5 to 6.

The "pH" in connection with the present invention is defined as the value which is measured at 25° C. after stirring for 5 minutes using a calibrated pH electrode in accordance with ISO 4319 (1977).

The present invention further provides the use of the polyglycerol esters according to the invention for aiding the microbiological stabilization of formulations.

The examples listed below describe the present invention by way of example, without any intention of restricting the invention, the scope of application of which is apparent from the entirety of the description and the claims, to the embodiments specified in the examples.

The following figures are a component of the examples:

EXAMPLES

Synthesis Example 1), According to the Invention

Synthesis Example 1a)

A mixture of glycerol (2102 g, 22.8 mol) and 45% strength aqueous potassium hydroxide solution (24.2 g) was heated to 240° C. at 400 mbar over the course of 1 hour and the water which formed was continuously distilled off. As soon as the reaction mixture had reached a refractive index of ≥1.4900 (typically after 20-21 h at 240° C.), the pressure was slowly reduced to 50 mbar and further water and excess glycerol were distilled off at 240° C. until the remaining mixture had a hydroxyl number of 880 mg KOH/g.

A mixture of the polyglycerol obtained in this way (554.8 g, 0.75 mol) and stearic acid and palmitic acid in the ratio 1:1 (477.1 g, 1.77 mol) was heated up to 240° C. over the course of 3 h with the introduction of nitrogen, and the mixture was then stirred at this temperature and the water which formed was continuously removed until an acid number of ≤10 was reached.

Synthesis Example 1b)

A mixture of glycerol (267.3 g, 2.90 mol) and caprylic acid (837.0 g, 5.79 mol) was heated up to 240° C. over the course of 3 h with the introduction of nitrogen, and the mixture was then stirred at this temperature and the water which formed was continuously removed until an acid number of ≤10 was reached.

Synthesis Example 1c)

A mixture of a polyglycerol ester obtained as described in Example 1a) (50 g) and of a polyglycerol ester obtained as described in Example 1b) (50 g) was heated up to 240° C. over the course of 3 h with the introduction of nitrogen, and the mixture was then stirred at this temperature and the water which formed was continuously removed until an acid number of ≤1.0 was reached.

The polyglycerol ester thus obtained releases, after its complete hydrolysis, per mole of polyglycerol ester
about 0.4 mol of stearic acid and palmitic acid in the ratio 1:1 and
about 1.4 mol of caprylic acid and
is characterized in that the polyglycerol released after complete hydrolysis of the polyglycerol ester has a mass ratio of glycerol to diglycerol of about 4. The polyglycerol obtained after complete hydrolysis has a degree of polymerization of about 3 and a content of polyglycerols with a degree of polymerization of 2 and greater of more than 60%, a content of polyglycerols with a degree of polymerization of 3 and greater of more than 50% and a content of polyglycerols with a degree of polymerization of 4 and greater of more than 40%.

Synthesis Example 2), According to the Invention

Synthesis Example 2a)

A mixture of glycerol (2102 g, 22.8 mol) and 45% strength aqueous potassium hydroxide solution (24.2 g) was heated to 240° C. at 400 mbar over the course of 1 hour and the water which formed was continuously distilled off. As soon as the reaction mixture had reached a refractive index of ≥1.4900 (typically after 20-21 h at 240° C.), the pressure was slowly reduced to 50 mbar and further water as well as excess glycerol were distilled off at 240° C. until the remaining mixture had a hydroxyl number of 880 mg KOH/g.

A mixture of the thus obtained polyglycerol (554.8 g, 0.75 mol) and stearic acid and palmitic acid in the ratio 1:1 (477.1 g, 1.77 mol) was heated up to 240° C. over the course of 3 h with the introduction of nitrogen, and the mixture was then stirred at this temperature and the water which formed was continuously removed until an acid number of ≤10 was reached.

Synthesis Example 2b)

A mixture of glycerol (267.3 g, 2.90 mol) and caprylic acid (767.9 g, 5.31 mol) was heated up to 240° C. over the course of 3 h with the introduction of nitrogen and the mixture was then stirred at this temperature and the water which formed was continuously removed until an acid number of ≤10 was reached.

Synthesis Example 2c)

A mixture of a polyglycerol ester obtained as described in Example 2a) (50 g) and of a polyglycerol ester obtained as described in Example 2b) (50 g) was heated up to 240° C. over the course of 3 h with the introduction of nitrogen, and the mixture was then stirred at this temperature and the water which formed was continuously removed until an acid number of ≤1.0 was reached.

The thus obtained polyglycerol ester releases, after its complete hydrolysis, per mole of polyglycerol ester about 0.4 mol of stearic acid and palmitic acid in the ratio 1:1 and about 1.3 mol of caprylic acid and is characterized in that the polyglycerol released after complete hydrolysis of the polyglycerol ester has a mass ratio of glycerol to diglycerol of about 4. The polyglycerol obtained after complete hydrolysis has a degree of polymerization of about 3 and a content of polyglycerols with a degree of polymerization of 2 and greater of more than 60%, a content of polyglycerols with a degree of polymerization of 3 and greater of more than 50% and a content of polyglycerols with a degree of polymerization of 4 and greater of more than 40%.

Synthesis Example 3), According to the Invention

A mixture of glycerol (2102 g, 22.8 mol) and 45% strength aqueous potassium hydroxide solution (24.2 g) was heated to 240° C. at 400 mbar over the course of 1 hour and the water which formed was continuously distilled off. As soon as the reaction mixture had reached a refractive index of ≥1.4900 (typically after 20-21 h at 240° C.), the pressure was slowly reduced to 50 mbar and further water as well as excess glycerol were distilled off at 240° C. until the remaining mixture had a hydroxyl number of 880 mg KOH/g.

A mixture of the thus obtained polyglycerol (147.0 g, 0.20 mol), glycerol (73.7 g, 0.8 mol) and stearic acid and palmitic acid in the ratio 1:1 (129.5 g, 0.48 mol) and caprylic acid (228.5 g, 1.58 mol) was heated up to 240° C. over the course of 3 h with the introduction of nitrogen, and the mixture was then stirred at this temperature and the water which formed was continuously removed until an acid number of ≤1.0 was reached.

The thus obtained polyglycerol ester releases, after its complete hydrolysis, per mole of polyglycerol ester about 0.5 mol of stearic acid and palmitic acid in the ratio 1:1 and about 1.6 mol of caprylic acid and is characterized in that the polyglycerol released after complete hydrolysis of the polyglycerol ester has a mass ratio of glycerol to diglycerol of about 4. The polyglycerol obtained after complete hydrolysis has a degree of polymerization of about 3 and a content of polyglycerols with a degree of polymerization of 2 and greater of more than 60%, a content of polyglycerols with a degree of polymerization of 3 and greater of more than 50% and a content of polyglycerols with a degree of polymerization of 4 and greater of more than 40%.

Synthesis Example 4), not According to the Invention

Synthesis Example 4a)

A mixture of glycerol (2102 g, 22.8 mol) and 45% strength aqueous potassium hydroxide solution (24.2 g) was heated to 240° C. at 400 mbar over the course of 1 hour and the water which formed was continuously distilled off. As soon as the reaction mixture had reached a refractive index of ≥1.4810, the pressure was slowly reduced to 50 mbar and further water as well as excess glycerol were distilled off at 240° C. until the remaining mixture had a hydroxyl number of 1150 mg KOH/g.

A mixture of the thus obtained polyglycerol (114.6 g, 0.48 mol) and stearic acid and palmitic acid in the ratio 1:1 (212.8 g, 0.79 mol) was heated up to 240° C. over the course of 3 h with the introduction of nitrogen and the mixture was then stirred at this temperature and the water which formed was continuously removed until an acid number of ≤10 was reached.

Synthesis Example 4b)

A mixture of glycerol (2102 g, 22.8 mol) and 45% strength aqueous potassium hydroxide solution (24.2 g) was heated to 240° C. at 400 mbar over the course of 1 hour and the water which formed was continuously distilled off. As soon as the reaction mixture had reached a refractive index of ≥1.4810, the pressure was slowly reduced to 50 mbar and further water and excess glycerol were distilled off at 240° C. until the remaining mixture had a hydroxyl number of 1150 mg KOH/g.

A mixture of the thus obtained polyglycerol (174.6 g, 0.73 mol) and caprylic acid (125.4 g, 0.86 mol) was heated up to 240° C. over the course of 2 h with the introduction of nitrogen, and the mixture was then stirred at this temperature and the water which formed was continuously removed until an acid number of ≤10 was reached.

Synthesis Example 4c)

A mixture of a polyglycerol ester obtained as described in Example 4a) (100 g) and of a polyglycerol ester obtained as described in Example 4b) (33.3 g) was heated to 240° C., and the mixture was then stirred at this temperature and the water which formed was continuously removed until an acid number of ≤1.0 was reached.

The thus obtained polyglycerol ester releases, after its complete hydrolysis, per mole of polyglycerol ester about 1.1 mol of stearic acid and palmitic acid in the ratio 1:1 and about 0.4 mol of caprylic acid and is characterized in that the polyglycerol released after complete hydrolysis of the polyglycerol ester has a mass ratio of glycerol to diglycerol of less than 1.5 and a degree of polymerization of about 3.

Synthesis Example 5), not According to the Invention

A mixture of glycerol (2102 g, 22.8 mol) and 45% strength aqueous potassium hydroxide solution (24.2 g) was heated to 240° C. at 400 mbar over the course of 1 hour, and the water which formed was continuously distilled off. As soon as the reaction mixture had reached a refractive index of ≥1.4810, the pressure was slowly reduced to 50 mbar and further water as well as excess glycerol were distilled off at 240° C. until the remaining mixture had a hydroxyl number of 1150 mg KOH/g.

A mixture of the thus obtained polyglycerol (99.5 g, 0.41 mol) and stearic acid and palmitic acid in the ratio 1:1 (50.0 g, 0.19 mol) and caprylic acid (50.0 g, 0.35 mol) was heated up to 240° C. over the course of 3 h with the introduction of nitrogen, and the mixture was then stirred at this temperature and the water which formed was continuously removed until an acid number of ≤3.0 was reached.

The thus obtained polyglycerol ester releases, after its complete hydrolysis, per mole of polyglycerol ester about 0.5 mol of stearic acid and palmitic acid in the ratio of 1:1 and about 0.9 mol of caprylic acid and is characterized in that the polyglycerol released after complete hydrolysis of the polyglycerol ester has a mass ratio of glycerol to diglycerol of less than 1.5 and a degree of polymerization of about 3.

Synthesis Example 6), not According to the Invention

A mixture of glycerol (2102 g, 22.8 mol) and 45% strength aqueous potassium hydroxide solution (24.2 g) was heated to 240° C. at 400 mbar over the course of 1 hour and the water which formed was continuously distilled off. As soon as the reaction mixture had reached a refractive index of ≥1.4810, the pressure was slowly reduced to 50 mbar and further water and excess glycerol were distilled off at 240° C. until the remaining mixture had a hydroxyl number of 1150 mg KOH/g.

A mixture of the thus obtained polyglycerol (180.1 g, 0.75 mol) and stearic acid and palmitic acid in the ratio 1:1 (234.7 g, 0.87 mol) was heated up to 240° C. over the course of 3 h with the introduction of nitrogen and the mixture was then stirred at this temperature and the water which formed was continuously removed until an acid number of ≤1.0 was reached.

The thus obtained polyglycerol ester releases, after its complete hydrolysis, per mole of polyglycerol ester about 1.2 mol of stearic acid and palmitic acid in the ratio 1:1 and is characterized in that the polyglycerol released after complete hydrolysis of the polyglycerol ester has a mass ratio of glycerol to diglycerol of less than 1.5 and a degree of polymerization of about 3.

Synthesis Example 7), not According to the Invention

A mixture of glycerol (2102 g, 22.8 mol) and 45% strength aqueous potassium hydroxide solution (24.2 g) was heated to 240° C. at 400 mbar over the course of 1 hour and the water which formed was continuously distilled off. As soon as the reaction mixture had reached a refractive index of ≥1.4810, the pressure was slowly reduced to 50 mbar and further water as well as excess glycerol were distilled off at 240° C. until the remaining mixture had a hydroxyl number of 1150 mg KOH/g.

A mixture of the thus obtained polyglycerol (180.1 g, 0.75 mol) and caprylic acid (126.0 g, 0.87 mol) was heated up to 240° C. over the course of 3 h with the introduction of nitrogen and the mixture was then stirred at this temperature and the water which formed was continuously removed until an acid number of ≤1.0 was reached.

The thus obtained polyglycerol ester releases, after its complete hydrolysis, per mole of polyglycerol ester about 1.2 mol of caprylic acid and is characterized in that the polyglycerol released after complete hydrolysis of the polyglycerol ester has a mass ratio of glycerol to diglycerol of less than 1.5 and a degree of polymerization of about 3.

Example 8) Emulsion Stability

All concentrations in the application examples are given in percent by weight. Customary homogenization processes known to the person skilled in the art were used to produce the emulsions.

The emulsions were therefore produced typically by heating oil phase and water phase to 70-75° C. Subsequently, either the oil phase was stirred into the water, or oil phase and water phase were combined without stirring. The mixture was then homogenized using a suitable homogenizer (e.g. Ultraturrax) for about 1-2 minutes.

Stabilizing polymers (e.g. carbomers) are preferably stirred into the emulsion as oil dispersion at temperatures of 50-60° C. The mixture is then briefly homogenized.

Addition of further ingredients (e.g. preservatives, active ingredients) was preferably carried out at 40° C. If the formulations were preserved with organic acids, the pH of the emulsions was adjusted to about 5.

These experiments are intended to show that the polyglycerol esters according to the invention have advantages with regard to emulsion stability. Various non-inventive emulsifiers from Examples 4 to 7 were selected here as representatives of polyglycerol-based O/W emulsifiers based on the prior art.

To test the storage stability of the emulsions, these were stored for three months at room temperature, 40° C. and 45° C. To assess the low-temperature stability, moreover, they were stored for one month at −5° C., and three freeze-thaw cycles of 25° C./−15° C./25° C. were carried out. Considerable changes in the appearance or the consistency, and in particular oil or water separations were weighted as criteria for instability.

The following formulation shows that the emulsifiers according to the invention in formulations a, b and c have advantages for the stabilization of typical cosmetic emulsions compared to the non-inventive emulsifiers in formulations d, e and g. A mixture f based on the prior art and comprising polyglycerol-based O/W emulsifier analogously to non-inventive synthesis Example 6 with standard commercial glyceryl caprylate is also unable to stabilize the emulsion in the desired manner.

| | Formulation 1 | | | | | | |
|---|---|---|---|---|---|---|---|
| | 1a | 1b | 1c | 1d | 1e | 1f | 1g |
| Inventive emulsifier according to Ex. 1 | 3.0 | | | | | | |

-continued

| | Formulation 1 | | | | | | |
|---|---|---|---|---|---|---|---|
| | 1a | 1b | 1c | 1d | 1e | 1f | 1g |
| Inventive emulsifier according to Ex. 2 | | 3.0 | | | | | |
| Inventive emulsifier according to Ex. 3 | | | 3.0 | | | | |
| Noninventive emulsifier according to Ex. 4 | | | | 3.0 | | | |
| Noninventive emulsifier according to Ex. 5 | | | | | 3.0 | | |
| Noninventive emulsifier according to Ex. 6 | | | | | | 1.5 | |
| Noninventive emulsifier according to Ex. 7 | | | | | | | 3.0 |
| Glyceryl Caprylate[1] | | | | | | 1.5 | |
| Almond oil | 6.0 | 6.0 | 6.0 | 6.0 | 6.0 | 6.0 | 6.0 |
| Caprylic/Capric Triglyceride[2] | 6.0 | 6.0 | 6.0 | 6.0 | 6.0 | 6.0 | 6.0 |
| Glycerol | 3.0 | 3.0 | 3.0 | 3.0 | 3.0 | 3.0 | 3.0 |
| Water | ad 100 | ad 100 | ad 100 | ad 100 | ad 100 | ad 100 | ad 100 |
| Carbomer[3] | 0.2 | 0.2 | 0.2 | 0.2 | 0.2 | 0.2 | 0.2 |
| Ethylhexyl Palmitate[4] | 0.8 | 0.8 | 0.8 | 0.8 | 0.8 | 0.8 | 0.8 |
| NaOH, 10% aq. | 0.6 | 0.6 | 0.6 | 0.6 | 0.6 | 0.6 | 0.6 |
| Phenoxyethanol | 0.8 | 0.8 | 0.8 | 0.8 | 0.8 | 0.8 | 0.8 |
| Emulsion stability | OK | OK | OK | NOK glassy, considerable coalescence | NOK Oil separation upon storage under warm conditions | NOK No emulsion formation | NOK No emulsion formation |

[1] Dermosoft GMCY (Dr. Straetmans GmbH)
[2] TEGOSOFT CT (Evonik Industries AG)
[3] TEGO Carbomer 141 (Evonik Industries AG)
[4] TEGOSOFT OP (Evonik Industries AG)

Example 9) Comparison of the Antimicrobial Stabilization of Cosmetic Emulsions Using a Conventional Preservative in Combination with Inventive or Noninventive Emulsifiers

| Formulation 2 | 2a | 2b | 2c | 2d |
|---|---|---|---|---|
| Inventive emulsifier according to Ex. 1 | 3.0 | | | |
| Inventive emulsifier according to Ex. 2 | | 3.0 | | |
| Noninventive emulsifier according to Ex. 4 | | | 3.0 | |
| Noninventive emulsifier according to Ex. 6 | | | | 3.0 |
| Almond oil | 6.0 | 6.0 | 6.0 | 6.0 |
| Caprylic/Capric Triglyceride[2] | 6.0 | 6.0 | 6.0 | 6.0 |
| Glycerol | 3.0 | 3.0 | 3.0 | 3.0 |
| Water | ad 100 | ad 100 | ad 100 | ad 100 |
| Carbomer[3] | 0.2 | 0.2 | 0.2 | 0.2 |
| Ethylhexyl Palmitate[4] | 0.8 | 0.8 | 0.8 | 0.8 |
| NaOH, 10% aq. | 0.6 | 0.6 | 0.6 | 0.6 |
| Phenoxyethanol | 0.5 | 0.5 | 0.5 | 0.5 |

Results of the microbiological loading test carried out in accordance with chapter 5.1.3 Testing adequate preservation in the European Pharmacopoeia, 4th Edition, Grundwerk 2002. The investigation was carried out with formulation 2 for the listed germs.

| Germs used | Inventive emulsifier according to Ex. 1 | Inventive emulsifier according to Ex. 2 | Noninventive emulsifier according to Ex. 4 | Noninventive emulsifier according to Ex. 6 |
|---|---|---|---|---|
| E. coli | OK | OK | OK | NOK |
| Cd. albicans | OK | OK | NOK | NOK |

The inventive emulsifiers according to Ex. 1 and 2 aid the effectiveness of the preservative, and therefore an adequate microbial stability for the listed germs can be achieved. This effect cannot be demonstrated for the noninventive emulsifiers according to synthesis Examples 4 and 6.

Formulation Examples

The examples below are intended to show that the polyglycerol esters according to the invention can be used in a large number of cosmetic formulations.

Moreover, with the help of the polyglycerol esters according to the invention, it is possible to stably incorporate pigments or solids into emulsion preparations.

Furthermore, the examples show good compatibility with typical emulsifiers, coemulsifiers, oils, thickeners and stabilizers, as well as good compatibility with emulsion-burdening ingredients such as UV filters, antimicrobial active ingredients or cosmetic active ingredients.

The examples are intended to illustrate the present invention without limiting it.

Formulation Example with Progress of the Germ Counts Over a Storage Time of Four Weeks Based on the Inventive Emulsifier According to Synthesis Example 1:

| Formulation | 3 |
|---|---|
| Inventive emulsifier according to Ex. 1 | 6.0 |
| Caprylic/capric triglyceride | 3.5 |
| Isopropyl Palmitate | 3.5 |
| C12-15 Alkyl Benzoate | 3.5 |
| Dimethicone | 3.5 |
| Glycerol | 10.0 |
| Acrylates/C10-30 alkyl acrylate crosspolymer | 0.2 |
| Alcohol | 3.0 |
| Water | ad 100 |
| Trisodium EDTA 20% aq. | 1.0 |
| pH (adjust to pH 6 with NaOH/citric acid etc.) | 6.0 |

Results of the microbiological loading test carried out according to DIN EN ISO 11930. For this experimental series, in addition to the test microorganisms listed in DIN EN ISO 11930, further species were used in order to evaluate the activity spectrum in more detail.

For the evaluation, the evaluation criteria according to DIN EN ISO 11930 were not used for the formulation, but the selective antimicrobial effect present against certain groups of microorganisms was evaluated. The test consists of the contamination of product samples with microorganisms (bacteria, yeast and fungi), as well as the determination of the living cell count (CFU/g) at the defined test time points 0d, 7d, 14d and 28d after contamination.

| Test germ (-mixture) | Germ count/g after | | | |
|---|---|---|---|---|
| | 0 d | 7 d | 14 d | 28 d |
| Staph. aureus | $2.7 \times 10^5$ | $<1.0 \times 10^2$ | $<1.0 \times 10^2$ | $<1.0 \times 10^2$ |
| Staph. epidermis | | | | |
| Ps. aueruginosa | $2.4 \times 10^5$ | $1.2 \times 10^3$ | $<1.0 \times 10^2$ | $<1.0 \times 10^2$ |
| Pseudomonas putida | | | | |
| Burkholderia cepacia | | | | |
| Escherichia coli | | | | |
| Enterobacter gergoviae | | | | |
| Serratia marcescens | | | | |
| Candida albicans | $2.2 \times 10^5$ | $<1.0 \times 10^2$ | $<1.0 \times 10^2$ | $<1.0 \times 10^2$ |
| Candida parapsilosis | | | | |
| Candida guilliermondii | | | | |
| Aspergillus brasiliensis | $2.9 \times 10^5$ | $>5.0 \times 10^4$ | $>5.0 \times 10^4$ | $<1.0 \times 10^2$ |

This example shows that the preserving effect of the amount of alcohol used can be increased by using the emulsifier according to the invention to the extent that the antimicrobial stability of the emulsion is ensured.

Cream Based on Sustainable Ingredients

| Formulation 4 | 4a | 4b | 4c |
|---|---|---|---|
| Inventive emulsifier according to Ex. 2 | 3.0 | 3.0 | 2.0 |
| Glyceryl Stearate SE | | 0.5 | |
| Polyglyceryl-3 Dicitrate/Stearate [5] | | | 1.0 |
| Cetearyl Alcohol | 1.3 | 1.3 | 1.3 |
| Glyceryl Stearate | 1.2 | 1.2 | 1.2 |
| Avocado oil | 6.0 | 6.0 | 6.0 |
| Caprylic/Capric Triglyceride | 8.5 | 8.5 | 8.5 |
| Oleyl Erucate [6] | 5.0 | 5.0 | 5.0 |
| Glycerol | 3.0 | 3.0 | 3.0 |
| Water | ad 100 | ad 100 | ad 100 |
| Xanthan Gum [7] | 0.2 | 0.2 | 0.2 |
| NaOH 10% aq. (pH adjustment to 5.0) | q.s. | q.s. | q.s. |
| Benzyl alcohol, glycerol, benzoic acid, sorbic acid [8] | 0.5 | 0.5 | 0.5 |

[5] TEGO Care PSC 3 (Evonik Industries AG)
[6] TEGOSOFT OER (Evonik Industries AG)
[7] Keltrol CG-SFT (CP Kelco)
[8] Rokonsal BSB-N (Ashland)

Thin-liquid lotion based on sustainable ingredients. Microbial stabilization of the emulsion without using substances listed in Annex 6 of the Cosmetics Ordinance.

| Formulation 5 | 5a | 5b | 5c |
|---|---|---|---|
| Inventive emulsifier according to Ex. 1 | 3.0 | 2.0 | 2.0 |
| Polyglyceryl-10 Stearate [9] | | 1.0 | |
| Glyceryl Stearate Citrate [10] | | | 1.0 |
| Glyceryl Stearate | 0.5 | 0.5 | 0.5 |
| Stearyl Alcohol | 0.5 | 0.5 | 0.5 |
| Almond oil | 5.0 | 5.0 | 5.0 |
| Isoamyl cocoate [11] | 5.5 | 5.5 | 5.5 |
| Caprylic/Capric Triglyceride [2] | 5.5 | 5.5 | 5.5 |
| Glycerol | 4.0 | 4.0 | 4.0 |
| Water | ad 100 | ad 100 | ad 100 |
| Xanthan Gum [7] | 0.5 | 0.5 | 0.5 |
| Ethanol | 10.0 | 10.0 | 10.0 |

[9] Polyaldo 10-1-S (Lonza Group AG)
[10] AXOL C 62 (Evonik Industries AG)
[11] TEGOSOFT AC (Evonik Industries AG)

Cream with Active Ingredients

| Formulation 6 | 6a | 6b | 6c |
|---|---|---|---|
| Inventive emulsifier according to Ex. 2 | 3.0 | 2.0 | 2.5 |
| Sodium Stearoyl Glutamate [12] | | 1.0 | |
| Sodium cetearyl sulphate [13] | | | 0.5 |
| Glyceryl Stearate | 1.5 | 1.5 | 1.5 |
| Stearyl Alcohol | 1.0 | 1.0 | 1.0 |
| Caprylic/Capric Triglyceride [2] | 10.0 | 10.0 | 10.0 |
| Ethylhexyl Palmitate [4] | 8.3 | 8.3 | 8.3 |
| Triisostearin [14] | 2.0 | 2.0 | 2.0 |
| Water | ad 100 | ad 100 | ad 100 |
| Hydrolyzed Hyaluronic Acid [15] | 0.1 | 0.1 | 0.1 |
| Glycerol | 3.0 | 3.0 | 3.0 |
| Carbomer [16] | 0.2 | 0.2 | 0.2 |
| NaOH 10% aq. | 0.6 | 0.6 | 0.6 |
| Terminalia Arjuna Bark Extract, Pentylene Glycol [17] | 2.0 | 2.0 | 2.0 |
| Phenoxyethanol | 0.5 | 0.5 | 0.5 |

[12] Eumulgin SG (BASF SE)
[13] Lanette E (BASF SE)
[14] TEGOSOFT TIS (Evonik Industries AG)
[15] HyaCare 50 (Evonik Industries AG)
[16] TEGO Carbomer 134 (Evonik Industries AG)
[17] TEGO Arjuna S (Evonik Industries AG)

Sunscreen Lotion SPF 20

| Formulation 7 | 7a | 7b | 7c | 7d |
|---|---|---|---|---|
| Inventive emulsifier according to Ex. 1 | 3.0 | 2.0 | 2.5 | 2.0 |
| Glyceryl Stearate Citrate [10] | | 1.0 | | 1.0 |
| Potassium Cetyl Phosphate | | | 0.5 | |
| Cetearyl Alcohol | 1.0 | 1.0 | 1.0 | 1.0 |
| Caprylic/Capric Triglyceride [2] | 2.8 | 2.8 | 2.8 | 1.5 |

| Formulation 7 | 7a | 7b | 7c | 7d |
|---|---|---|---|---|
| Oleyl Erucate [6] | 2.0 | 2.0 | 2.0 | 1.0 |
| C12-15 Alkyl Benzoate | | | | 3.0 |
| Ethylhexyl salicylate | 5.0 | 5.0 | 5.0 | 5.0 |
| Titanium Dioxide; Diethylhexyl Carbonate; Polyglyceryl-6 Polyhydroxystearate [19] | 8.9 | 8.9 | 8.9 | 8.9 |
| Octocrylene | 8.0 | 8.0 | 8.0 | 8.0 |
| Bis-Ethylhexyloxyphenol Methoxyphenyl Triazine [20] | 1.5 | 1.5 | 1.5 | 1.5 |
| Butyl methoxydibenzoylmethane | 1.7 | 1.7 | 1.7 | 1.7 |
| Tocopheryl acetate | 0.5 | 0.5 | 0.5 | 0.5 |
| Glycerol | 3.0 | 3.0 | 3.0 | 3.0 |
| Water | ad 100 | ad 100 | ad 100 | ad 100 |
| Carbomer [3] | 0.2 | 0.2 | 0.2 | 0.2 |
| NaOH 10% aq. | 0.5 | 0.5 | 0.5 | 0.5 |
| Methylisothiazolinone, Methylparaben, Ethylparaben; Dipropylene Glycol [21] | 0.5 | 0.5 | 0.5 | 0.5 |

[19] TEGO SUN TDEC 45 (Evonik Industries AG)
[20] Tinosorb S (BASF SE)
[21] Microcare MEM (Thor)

Natural Make-Up Foundation

| Formulation 8 | 8a | 8b |
|---|---|---|
| Inventive emulsifier according to Ex. 1 | 4.0 | 3.0 |
| Polyglyceryl-6 Stearate; Polyglyceryl-6 Behenate [22] | | 2.0 |
| Cetearyl Alcohol | 1.5 | 1.5 |
| Glyceryl Stearate | 1.5 | 1.5 |
| Myristyl Myristate [23] | 2.0 | 2.0 |
| Isoamyl Cocoate [11] | 6.0 | 6.0 |
| Decyl Cocoate [24] | 7.0 | 7.0 |
| Water | ad 100 | ad 100 |
| Glycerol | 1.0 | 1.0 |
| Magnesium Aluminum Silicate [25] | 0.8 | 0.8 |
| Xanthan Gum [7] | 0.2 | 0.2 |
| Titanium Dioxide [26] | 8.0 | 8.0 |
| Iron Oxides [27] | 0.9 | 0.9 |
| Iron Oxides [28] | 0.2 | 0.2 |
| Iron Oxides [29] | 0.4 | 0.4 |
| Iron Oxides [30] | 0.1 | 0.1 |
| Glycerin; Aqua; Sodium levulinate; Sodium anisate [31] | 1.5 | 1.5 |
| Glyceryl caprylate [1] | 0.2 | 0.2 |
| Citric Acid 20% aq. | 0.5 | 0.5 |
| Cellulose [32] | 2.0 | 2.0 |

[22] TEGO Care PBS 6 (Evonik Industries AG)
[23] TEGOSOFT MM (Evonik Industries AG)
[24] TEGOSOFT DC (Evonik Industries AG)
[25] Veegum Ultra (Vanderbilt Minerals)
[26] Kronos 1171 (Kronos Systems)
[27] Sicovit Gelb 10E (Rockwood Pigments)
[28] Sicovit Rot 30E (Rockwood Pigments)
[29] Sicovit Braun 70E (Rockwood Pigments)
[30] Sicovit Schwarz 80E (Rockwood Pigments)
[31] Dermosoft 1388 ECO (Dr. Straetmans GmbH)
[32] TEGO Feel Green (Evonik Industries AG)

Cream

| Formulation 9 | 9a | 9b | 9c |
|---|---|---|---|
| Inventive emulsifier according to Ex. 3 | 3.0 | 2.5 | 2.0 |
| Cetearyl Glucoside | | 0.5 | |
| Polyglyceryl-6 Distearate | | | 1.0 |
| Glyceryl Stearate | 4.0 | 4.0 | 4.0 |
| Cetearyl Alcohol | 2.0 | 2.0 | 2.0 |
| Avocado oil | 8.0 | 8.0 | 8.0 |
| Isopropyl Myristate [33] | 8.0 | 8.0 | 8.0 |
| Glycerol | 2.0 | 2.0 | 2.0 |
| Xanthan Gum [7] | 0.2 | 0.2 | 0.2 |
| Glycerol | 1.0 | 1.0 | 1.0 |
| Water | ad 100 | ad 100 | ad 100 |
| Phenoxyethanol; Benzoic Acid; Dehydroacetic Acid [34] | 0.5 | 0.5 | 0.5 |
| NaOH 10% aq. (pH adjustment to 5.5) | q.s. | q.s. | q.s. |

[33] TEGOSOFT M (Evonik Industries AG)
[34] Rokonsal ND (Ashland)

Deodorant

| Formulation 10 | 10a | 10b | 10c |
|---|---|---|---|
| Inventive emulsifier according to Ex. 2 | 3.0 | 1.5 | 1.5 |
| Methylglucose Sesquistearate [35] | 1.0 | 1.5 | 1.5 |
| Diethylhexyl Carbonate [36] | 3.5 | 3.5 | 3.0 |
| PPG-14 Butyl Ether [37] | 3.5 | 3.5 | |
| Isopropyl Palmitate | | | 3.0 |
| Hydroxypropyl Starch Phosphate [38] | 4.0 | 4.0 | 4.0 |
| Water | ad 100 | ad 100 | ad 100 |
| Polyglyceryl-3 Caprylate [39] | 0.5 | 0.5 | 0.5 |
| Phenoxyethanol | 0.7 | 0.7 | 0.7 |

[35] TEGO Care PS (Evonik Industries AG)
[36] TEGOSOFT DEC (Evonik Industries AG)
[37] TEGOSOFT PBE (Evonik Industries AG)
[38] Structure XL (AkzoNobel)
[39] TEGO Cosmo P 813 (Evonik Industries AG)

Antiperspirant/Deodorant Formulation

| Formulation 11 | 11a | 11b | 11c |
|---|---|---|---|
| Inventive emulsifier according to Ex. 1 | 3.0 | 2.0 | 3.0 |
| Methylglucose Sesquistearate [35] | 1.0 | 1.5 | |
| Polyglyceryl-4 Laurate [40] | | 0.5 | |
| Steareth-2 [41] | | | 2.0 |
| Steareth-20 [42] | | | 1.0 |
| Caprylic/Capric Triglyceride [2] | 3.5 | 3.5 | |
| Isopropyl Myristate [33] | 3.5 | 3.5 | |
| PPG-15 Stearyl Ether [43] | | | 3.0 |
| Phenoxyethyl Caprylate [44] | | | 4.0 |
| Hydroxyethyl Cellulose [45] | 0.5 | 0.5 | |
| Water | ad 100 | ad 100 | ad 100 |
| Aluminum Chlorohydrate (50% aq.) | 15.0 | 15.0 | 20.0 |
| Phenoxyethanol | 0.5 | 0.5 | 0.5 |

[40] TEGO Care PL 4 (Evonik Industries AG)
[41] TEGO Alkanol S 2 Pellets (Evonik Industries AG)
[42] TEGO Alkanol S 20 P (Evonik Industries AG)
[43] TEGOSOFT E (Evonik Industries AG)
[44] TEGOSOFT XC (Evonik Industries AG)
[45] Natrosol 250 HHR (Ashland Inc.)

The invention claimed is:
1. A polyglycerol ester which, after its complete hydrolysis, releases on average (number-average) per mole of polyglycerol ester from 1.1 to 4 mol of at least one carboxylic acid having 8 to 24 carbon atoms, the at least one carboxylic acid comprising
from 0.1 to 1.5 mol of at least one first carboxylic acid having 14 to 24 carbon atoms and,
from 0.5 to 3.9 mol of at least one second carboxylic acid having 6 to 12 carbon atoms are released,
wherein, following complete hydrolysis of the polyglycerol ester, a polyglycerol is obtained in which the mass ratio of glycerol to diglycerol is greater than 1.5.

2. The polyglycerol ester according to claim 1, wherein the polyglycerol obtained after complete hydrolysis of the polyglycerol ester has an average degree of polymerization of from 1.5 to 10, and
comprises at least 50% by weight of polyglycerols with a degree of polymerization of 2 and greater,
at least 40% by weight of polyglycerols with a degree of polymerization of 3 and greater and,
at least 30% by weight of polyglycerols with a degree of polymerization of 4 and greater,
where the percentages by weight refer to the total content of polyglycerol.

3. The polyglycerol ester according to claim 1, wherein the molar ratio of the first carboxylic acid obtained after complete hydrolysis of the polyglycerol ester to the second carboxylic acid is between 1:1.5 and 1:5.0.

4. The polyglycerol ester according to claim 1, wherein the first and the second carboxylic acid is selected from linear, saturated, unsubstituted carboxylic acids.

5. A polyglycerol ester which, after its complete hydrolysis, releases on average (number-average) per mole of polyglycerol ester from 1.1 to 4 mol of at least one carboxylic acid having 8 to 24 carbon atoms, the at least one carboxylic acid comprising
from 0.1 to 1.5 mol of a mixture of stearic acid and palmitic acid, and
from 0.5 to 3.9 mol of caprylic acid,
wherein, following complete hydrolysis of the polyglycerol ester, a polyglycerol is obtained in which the mass ratio of glycerol to diglycerol is greater than 1.5.

6. A process for producing a polyglycerol ester comprising the process steps
A) provision of a polyglycerol in which the mass ratio of glycerol to diglycerol is greater than 1.5,
B) esterification of at least one part of the polyglycerol with at least one first carboxylic acid having 14 to 24 carbon atoms and at least one second carboxylic acid having 6 to 12 carbon atoms, and
where the molar ratio of the first carboxylic acid used in process step B) to polyglycerol used in process step A) is from 0.1:1 to 1.5:1 and the molar ratio of the second carboxylic acid used in process step B) to polyglycerol used in process step A) is from 0.5:1 to 3.9:1.

7. The process according to claim 6,
where the molar ratio of the first carboxylic acid used in process step B) to polyglycerol used in process step A) is from 0.2:1 to 1.0:1 and the molar ratio of the second carboxylic acid used in process step B) to polyglycerol used in process step A) is from 0.8:1 to 2.5:1.

8. The process according to claim 6, wherein the polyglycerol provided in process step A) has an average degree of polymerization of from 1.5 to 10 and,
comprises at least 50% by weight of polyglycerols with a degree of polymerization of 2 and greater,
at least 40% by weight of polyglycerols with a degree of polymerization of 3 and greater and,
at least 30% by weight of polyglycerols with a degree of polymerization 4 and greater,
where the percentages by weight refer to the total content of polyglycerol.

9. The process according to claim 7, wherein in process step B) the first carboxylic acid used is a mixture of stearic acid and palmitic acid and the second carboxylic acid used is caprylic acid.

10. The polyglycerol ester according to claim 1, wherein, following complete hydrolysis of the polyglycerol ester, a polyglycerol is obtained in which the mass ratio of glycerol to diglycerol is greater than 2.

11. The polyglycerol ester according to claim 1, wherein, following complete hydrolysis of the polyglycerol ester, a polyglycerol is obtained in which the mass ratio of glycerol to diglycerol is greater than 3.

12. The polyglycerol ester according to claim 1, wherein, after its complete hydrolysis, on average (number-average) per mole of polyglycerol ester from 0.1 to 1.5 mol of at least one first carboxylic acid having 14 to 24 carbon atoms and from 0.5 to 3.9 mol of at least one second carboxylic acid having 6 to 12 carbon atoms are released.

13. The polyglycerol ester according to claim 1, wherein, after its complete hydrolysis, on average (number-average) per mole of polyglycerol ester from 0.2 to 1.0 mol of at least one first carboxylic acid having 14 to 24 carbon atoms and from 0.8 to 2.5 mol of at least one second carboxylic acid having 6 to 12 carbon atoms are released.

14. The polyglycerol ester according to claim 1, wherein, after its complete hydrolysis, on average (number-average) per mole of polyglycerol ester from 0.3 to 0.7 mol of at least one first carboxylic acid having 14 to 24 carbon atoms and from 1.0 to 2.0 mol of at least one second carboxylic acid having 6 to 12 carbon atoms are released.

15. The polyglycerol ester according to claim 1, wherein the polyglycerol obtained after complete hydrolysis of the polyglycerol ester has an average degree of polymerization of from 1.7 to 6, and
comprises at least 60% by weight of polyglycerols with a degree of polymerization of 2 and greater,
at least 50% by weight of polyglycerols with a degree of polymerization of 3 and greater and,
at least 40% by weight of polyglycerols with a degree of polymerization of 4 and greater,
where the percentages by weight refer to the total content of polyglycerol.

16. The polyglycerol ester according to claim 1, wherein the polyglycerol obtained after complete hydrolysis of the polyglycerol ester has an average degree of polymerization of from 2 to 3.5, and
comprises at least 60% by weight of polyglycerols with a degree of polymerization of 2 and greater,
at least 50% by weight of polyglycerols with a degree of polymerization of 3 and greater and,
at least 40% by weight of polyglycerols with a degree of polymerization of 4 and greater,
where the percentages by weight refer to the total content of polyglycerol.

17. The polyglycerol ester according to claim 1, wherein the molar ratio of the first carboxylic acid obtained after complete hydrolysis of the polyglycerol ester to the second carboxylic acid is between 1:2.0 and 1:4.0.

18. The polyglycerol ester according to claim 1, wherein the molar ratio of the first carboxylic acid obtained after complete hydrolysis of the polyglycerol ester to the second carboxylic acid is between 1:2.5 and 1:3.0.

19. The process according to claim 8, wherein in process step B) the first carboxylic acid used is a mixture of stearic acid and palmitic acid and the second carboxylic acid used is caprylic acid.

* * * * *